United States Patent
Neunhoeffer et al.

[11] Patent Number: 5,380,340
[45] Date of Patent: Jan. 10, 1995

[54] HAIR DYE CONTAINING AMINOPYRAZOLE DERIVATIVES AS WELL AS PYRAZOLE DERIVATIVES

[75] Inventors: Hans Neunhoeffer, Mühltal/FRG; Stefan Gerstung, Reinheim/FRG; Thomas Clausen; Wolfgang R. Balzer, both of Alsbach/FRG, all of Germany

[73] Assignee: Wella Aktiengesellschaft, Darmstadt, Germany

[21] Appl. No.: 27,171

[22] PCT Filed: Aug. 19, 1992

[86] PCT No.: PCT/EP92/01887

§ 371 Date: Mar. 4, 1993

§ 102(e) Date: Mar. 4, 1993

[87] PCT Pub. No.: WO93/07849

PCT Pub. Date: Apr. 29, 1993

[30] Foreign Application Priority Data

Oct. 14, 1991 [DE] Germany ............... 4133957

[51] Int. Cl.$^6$ ............ A61K 7/13; C07D 487/02
[52] U.S. Cl. .................... 8/409; 8/405; 8/406; 8/407; 8/408; 8/410; 8/414; 8/415; 8/423; 544/281; 548/303.1
[58] Field of Search ............ 8/405, 406, 407, 408, 8/409, 423, 410, 414, 415; 544/281; 548/303.1

[56] References Cited

U.S. PATENT DOCUMENTS

| | | | |
|---|---|---|---|
| 4,093,617 | 6/1978 | Robins et al. | 544/281 |
| 4,500,630 | 2/1985 | Sato et al. | 430/386 |
| 5,215,982 | 6/1993 | Sakane et al. | 514/202 |
| 5,234,818 | 8/1993 | Zimmerman et al. | 435/28 |

FOREIGN PATENT DOCUMENTS

| | | |
|---|---|---|
| 0264773 | 4/1988 | European Pat. Off. . |
| 3843892 | 6/1990 | Germany . |
| 9204883 | 4/1992 | WIPO . |

OTHER PUBLICATIONS

A. J. Goddart et al, Anti-Cancer Drug Design, Feb. 4, 1987, pp. 235–245.

A. J. Goddard, et al., Anti-Cancer Drug Design 2, Feb. 4, 1987, p. 235.

*Primary Examiner*—Paul Lieberman
*Assistant Examiner*—Caroline L. Dusheck
*Attorney, Agent, or Firm*—Michael J. Striker

[57] ABSTRACT

The composition for oxidative dyeing of hair contains at least one coupler and 0.010 to 3.0 percent by weight of at least one developer selected from the group consisting of aminopyrazole derivatives of the formula (I):

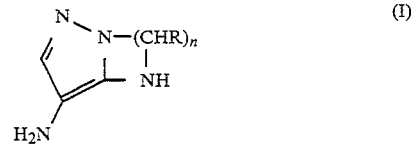

wherein R is selected from the group consisting of hydrogen and alkyl groups having one to four carbon atoms; n=2 or 3; and physiologically tolerated, water-soluble salts thereof. The developer and coupler substances are present in the composition in a total amount of from 0.1 to 5.0 percent. New pyrazole derivative compounds are also part of the invention.

13 Claims, No Drawings

HAIR DYE CONTAINING AMINOPYRAZOLE DERIVATIVES AS WELL AS PYRAZOLE DERIVATIVES

BACKGROUND OF THE INVENTION

The invention relates to compositions for the oxidative dyeing of keratin fibers based on aminopyrazole derivatives as well as new pyrazole derivatives.

Oxidative dyes have achieved considerable importance in the dyeing of hair. The dyeing is brought about by the reaction of certain developers with certain couplers in the presence of a suitable oxidizing agent.

In particular, 2,5-diaminotoluene, 2,5-diaminophenylethyl alcohol, p-aminophenol and 1,4-diaminobenzene are used as developers. Resorcinol, 4-chlororesorcinol, 1-naphthol, 5-amino-2-methylphenol and derivatives of m-phenylenediamine are included among those couplers whose use is preferred.

Oxidative dyestuffs used for dyeing human hair are subject to numerous special requirements. For example, they must be unobjectionable in toxicological and dermatological respects and must enable the desired intensity of coloring. In addition, a favorable fastness to light, permanent waving, acids and rubbing are demanded of the achieved hair dyes. But, in every instance, such hair dyes must remain stable over a period of at least 4 to 6 weeks without being influenced by light, rubbing or chemical agents. Moreover, it is necessary that a wide assortment of various color shades can be produced by combining suitable developers and couplers. In particular, 4-aminophenol, by itself or in a mixture with other developers, is used in combination with suitable couplers to achieve natural and especially fashionable shades in the red range.

The developer 4-aminophenol which was chiefly used formerly for the red range of the color scale has recently been criticized with respect to its physiological tolerability, while more recently recommended developers such as pyrimidine derivatives are not entirely satisfactory with respect to coloring. The pyrazole derivatives described in DE-OS 21 60 317, e.g. 3-amino-1-phenyl-2-pyrazolone-5, provide only a shallow depth of color which is unusable in hair dyeing practice.

The 4,5-diaminopyrazoles described in DE-OS 38 42 892 are satisfactory with respect to color intensity, but they show disadvantages which impede their use as hair dyes, e.g. 3(5), 4-diaminopyrazole shows a slight sensitizing activity. Because mixtures of isomers, which can only be separated by chromatography, are produced during their production other compounds, e.g. 4,5-diamino-1-methylpyrazole or 4,5-diamino-1-benzylpyrazole, are difficult to prepare.

Therefore, it is an object of the present invention to provide an oxidative hair dye composition based on a combination of developers and couplers containing a developer for the red range which is very favorably tolerated physiologically, is simple to produce and, together with conventional couplers, dyes the hair in brilliant red color hues with a great depth of color.

It has now been found that the proposed problem is solved in an outstanding manner by a composition for the oxidative dyeing of hair based on a combination of developers and couplers containing an aminopyrazole derivative of the general formula (I)

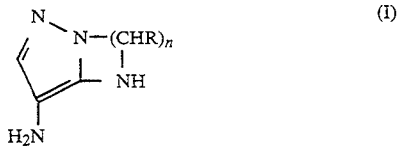

or its physiologically tolerated, water-soluble salts as developer, where R=hydrogen or an alkyl group containing from 1 to 4 carbon atoms and n=2 or 3.

The developers of formula (I), of which the 3-amino-4,5,6,7-tetrahydropyrazolo[1,5-a]pyrimidine (R=H, n=3), the 7-amino-2,3-dihydro-1H-imidazo[1,2-b]pyrazole (R=H, n=2), and the 3-amino-6-methyl-4,5,6,7-tetrahydropyrazolo[1,5-a]pyrimidine (R=CH$_3$, n=3) are preferred, are to be contained in the hair dye composition in a quantity of approximately 0.01 to 3.0 percent by weight, preferably in a quantity of 0.1 to 2.5 percent by weight.

Although it would appear obvious in view of the advantageous characteristics of the novel developers described here to use them as the only developers, it is also possible, of course, to use the developers of formula (I) together with known developers such as 1,4-diaminobenzene, 2,5-diaminotoluene or 2,5-diaminophenylethyl alcohol.

The following known couplers are preferred for use as constituents of the hair dye composition described here: resorcinol, 4-chlororesorcinol, 4,6-dichlororesorcinol, 2-methylresorcinol, 2-amino-4-(2'-hydroxyethyl)aminoanisole, 2,4-diaminobenzyl alcohol, 2,4-diaminophenylethyl alcohol, m-phenylenediamine, 2,4-diamino-5-(2'-hydroxyethoxy)toluene, 5-amino-2-methylphenol, 5-amino-4-fluoro-2-methylphenol, 5-amino-2-ethyl-4-fluorophenol, 5-amino-4-methoxy-2-methylphenol, 2,4-diaminophenoxyethanol, 4-amino-2-hydroxyphenoxyethanol, 1-naphthol, 3-aminophenol, 3-amino-2-methylphenol, 4-hydroxy-1,2-methylenedioxybenzene, 4-amino-1,2-methylenedioxybenzene, 4-(2'-hydroxyethyl)amino-1,2-methylenedioxybenzene, 2,4-diaminophenetole, 2,4-diamino-5-methylphenetole, 4-hydroxyindole, 3-amino-5-hydroxy-2,6-dimethoxypyridine, and 3,5-diamino-2,6-dimethoxypyridine.

The coupler and developers can be contained in the hair dye composition individually or in combination.

The total quantity of combined developers and couplers contained in the hair dye composition described here is 0.1 to 5.0 percent by weight, preferably 0.5 to 4.0 percent by weight.

The developer components are generally used in approximately equimolar quantities with respect to the coupler components. However, it is not disadvantageous if the quantity of developers is somewhat larger or smaller.

Further, the hair dye composition, according to the invention, can contain other dye components in addition, e.g. 6-amino-2-methylphenol and 2-amino-5-methylphenol, as well as other conventional direct-dyeing dyestuffs, e.g. triphenylmethane dyes such as 4-[(4'-aminophenyl)-(4''-imino-2'',5''-cyclohexadiene-1''-ylidine)-methyl]-2-methyl-aminobenzene monohydrochloride or Diamond Fuchsine (C.I. 42,510) and 4-[(4'-amino-3'-methylphenyl)-(4''-imino-3''-methyl-2'',5''-cyclohexadiene-1''-ylidene-methyl]-2-methyl-amino-benzene-monohydrochloride or Leather Ruby HF (C.I. 42,520), aromatic nitro dyes such as 2-nitro-1,4-diaminobenzene, 2-amino-4-nitrophenol, 2-amino-5-nitrophenol, 2-amino-4,6-dinitrophenol, 2-amino-5(2'-hydroxyethyl)aminonitrobenzene, and 2-methylamino-5bis(2'-hydroxyethyl)aminonitrobenzene, azo dyes such as the sodium salt of 7-[4'-amino-phenylazo]-8-hydroxynaphthaline-4-sulfonic acid or Acid Brown 4 (C.I. 14,805) and dispersed dyes such as 1,4-diaminoanthraquinone and 1,4,5,8-tetraaminoanthraquinone. The hair dye composition can contain these dye components in a quantity of approximately 0.1 to 4.0 percent by weight.

Of course, the couplers and developers as well as the other dye components, insofar as they are bases, can also be used in the form of physiologically tolerated salts with organic or inorganic acids such as hydrochloric acid or sulfuric acid, or—insofar as they have aromatic OH groups—in the form of salts with bases, e.g. as alkali phenolates.

Moreover, other conventional cosmetic ingredients can also be contained in the hair dye composition, e.g. antioxidants such as ascorbic acid, thiogylcolic acid or sodium sulfite, as well as perfume oils, complexing agents, wetting agents, emulsifiers, thickeners and hair care materials.

The preparation form of the novel hair dye composition can be e.g. a solution, particularly an aqueous or aqueous-alcoholic solution. But the particularly preferred preparation forms are a cream, gel or emulsion. Its composition is a mixture of dye components and conventional ingredients for such preparations.

Conventional ingredients in solutions, creams, emulsions or gels are e.g. solvents such as water, lower aliphatic alcohols, e.g. ethanol, propanol, isopropanol, glycerol or glycols such as 1,2-propylene glycol, wetting agents or emulsifiers from the classes of anionic, cationic, amphoteric or nonionic surface-active substances such as fatty alcohol sulfates, ethoxylated fatty alcohol sulfates, alkyl sulfonates, alkylbenzene sulfonates, alkylbenzene sulfonates, alkyltrimethylammonium salts, alkyl betaines, ethoxylated fatty alcohols, ethoxylated nonylphenols, fatty acid alkanol amides, ethoxylated fatty acid esters, also thickeners such as higher fatty alcohols, starch, cellulose derivatives, vaseline, paraffin oil and fatty acids, as well as hair care materials such as cationic resins, lanolin derivatives, cholesterol, pantothenic acid and betaine. The aforementioned components are used in quantities which are conventional for such purposes. For example, the wetting agents and emulsifiers are used in concentrations of approximately 0.5 to 30 percent by weight, the thickeners are used in quantities of approximately 0.1 to 25 percent by weight, and the hair care materials are used in a concentration of approximately 0.1 to 5.0 percent by weight.

Depending on the composition, the hair dye composition, according to the invention, can react in a slightly acidic, neutral or alkaline manner. In particular, it has a pH between 8.0 and 11.5, and it is preferably adjusted with ammonia. However, organic amines such as monoethanolamine and triethanolamine, or inorganic bases such as sodium hydroxide and potassium hydroxide can also be used.

When used for the oxidative dyeing of hair, the hair dye composition described above is mixed immediately prior to use with an oxidizing agent and a quantity of this mixture sufficient for the hair dyeing treatment, generally approximately 60 to 200 g depending on the fullness of the hair, is applied to the hair. Hydrogen peroxide or its addition compounds in urea, melamine or sodium borate in the form of a 3- to 12-percent, preferably a 6-percent aqueous solution chiefly come under consideration as oxidizing agents for developing the hair dye. If a 6-percent hydrogen peroxide solution is used as oxidizing agent, the weight ratio of hair dye composition to oxidizing agent is 5:1 to 1:2, but preferably 1:1. Larger quantities of oxidizing agent are used in the hair dye composition chiefly with higher concentrations of dyestuff or when a more intensive bleaching of hair is intended simultaneously. The mixture is allowed to act on the hair at 15° to 30° C. for approximately 10 to 45 minutes, preferably 30 minutes; the hair is then rinsed with water and dried. The hair is washed with a shampoo after this rinse, if necessary, and possibly re-rinsed with a weak organic acid such as citric acid or tartaric acid. The hair is then dried.

The production of the developers according to the invention has not yet been described in publications.

The production of 7-nitro-2,3-dihydro-1H-imidazo-[1,2-b]pyrazole is described in A. J. Goddard et al., *Anti Cancer Drug Design* 2, 235 (1987). It is based on a 5-amino-4-cyano-1-(2'-hydroxyethyl)pyrazole, from which the desired compound is obtained after ring closure and subsequent nitration with a yield of approximately 10%.

On the other hand, a better yield is obtained by alkylation with dibromoalkanes and subsequent reduction of the nitro group of the 3(5)-amino-4-nitropyrazole described in H. Dorn et al., *Liebigs-Ann. Chem.* 707 (1967), 141–146.

The compounds according to the invention can be produced in a manner analogous to the method described above.

The developers of formula (I) are used in the hair dye composition either as free bases or in the form of their physiologically tolerated salts with inorganic or organic acids, e.g. hydrochloric acid, sulfuric acid, phosphoric acid, acetic acid, propionic acid, lactic acid or citric acid. The compounds of formula (I) have good solubility in water. Moreover, they have an excellent shelf stability, particularly as constituents of the hair dye composition described here.

The hair dye composition, according to the invention, containing aminopyrazole derivatives as developers makes it possible to dye hair with excellent color fastness, particularly with respect to light, washing and rubbing, and the hair dyes can be removed again with reducing agents.

With respect to dyeing characteristics, the hair dye composition according to the invention offers possibilities reaching far beyond the substitution of conventionally used 4-aminophenols. It can produce brilliant red hues with extraordinary depth of color which cannot be achieved with current dye components. But apart from this application in the field of high fashion, natural color hues can also be produced by combining it with suitable couplers without requiring an additional developer of the p-phenylenediamine type.

The very good dyeing properties of the hair dye composition according to the present application can also be seen in that this composition makes it possible to dye gray hair that has not been chemically damaged beforehand easily and with good covering power.

The subject matter of the present patent application is further directed to novel pyrazole derivatives of the general formula (II)

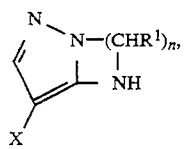

(II)

where $R^1$ is hydrogen or an alkyl group containing from 1 to 4 carbon atoms, $n=2$ or 3, and X is a nitro or amino group, where 7-amino-2,3-dihydro-1H-imidazo[1,2-b]pyrazole, 3-nitro-4,5,6,7-tetrahydropyrazolo[1,5-a]pyrimidine, 3-amino-4,5,6,7-tetrahydro-pyrazolo[1,5-a]pyrimidine, 3-nitro-6-methyl-4,5,6,7-tetrahydropyrazolo[1,5-a]pyrimidine, and 3-amino-6-methyl-4,5,6,7-tetrahydropyrazolo[1,5-a]pyrimidine are mentioned in particular.

The subject matter of the invention is explained in more detail in the following examples.

PRODUCTION EXAMPLES

EXAMPLE 1

Production of 3-amino-4,5,6,7-tetrahydropyrazolo[1,5-a]pyrimidine

Step 1: Synthesis of 3-nitro-4,5,6,7-tetrahydropyrazolo[1,5-a]pyrimidine

A solution of 51.2 g (0.4 moles) 3-amino-4-nitropyrazole in 650 ml dried DMF is slowly added by drops to a suspension of 10 g (0.4 moles) sodium hydride in 200 ml dried DMF. After the reaction is concluded, 121 g (0.6 moles) 1,3-dibromopropane in 250 ml DMF are added. The mixture is then heated for 5 hours accompanied by reflux. After cooling, the preparation is reduced to dryness. When the residue is treated with 300 ml dichloromethane and subsequently cooled to 0° C. the product is precipitated out together with NaBr. The raw product is recrystallized from 1200 ml ethanol. 59 g (38%) ocher-colored crystals with a melting point of 251°–252° C. are obtained.

$^1$H-NMR (DMSO-d$_6$, 60 MHz): $\delta=7.89$ (s,1H, —NH, exchangeable with D$_2$O), 7.85 (s, 1H, 3-H), 3.99 (t, 2H, J=7 Hz, 1N—CH$_2$—), 3.35 (mm, 2H, —NH—CH$_2$—CH$_2$) and 2.03 ppm (m, 2H, —CH$_2$—CH$_2$—CH$_2$).

MS (70 eV): m/e=168 (M+)

Step 2: Synthesis of 3-amino-4,5,6,7-tetrahydropyrazolo[1,5-a]pyrimidine 0.6 g (3.57 mmoles) 3-nitro-4,5,6,7-tetrahydropyrazolo [1,5-a]pyrimidine are hydrated in 130 ml methanol with 0.1 g Pd/C (10-percent) for 2 days at 25° C. and 50 bar. After removing the catalyst by filtration, the filtrate is treated with methanolic HCl and reduced. The precipitated product is removed by suction and washed with a little methanol. The compound is in the form of trihydrochloride hydrate which has a melting point of 179°–182° C. If the filtrate is mixed with an equimolar quantity of sulfuric acid after removal of the catalyst by filtration, the compound is obtained in the form of the sulfate with a melting point of 176°–179° C. after preparation.

$^1$H-NMR (DMSO-d$_6$, 60 MHz): $\delta=9.50$ (s, wide, 8H, —NH$_2$, HCl, H$_2$O exchangeable with D$_2$O), 7.75 (s, 1H, 3-H), 4.10 (t, 2H, J=7 Hz, 1N—CH$_2$), 3.29 (t, 2H, J=7 Hz, NH—CH$_2$—CH$_2$) and 2.02 ppm (m, 2H, —CH$_2$—CH$_2$—CH$_2$).

MS (70 eV): m/e=138 (M+)

EXAMPLE 2

Production of 7-amino-2,3-dihydro-1H-imidazo[1,2-b]pyrazole hydrosulfate 0.15 g (0.97 mmoles) 3-nitro-2,3-dihydro-1H-imidazo[1,2-b]pyrazole are hydrated as in Example 1, Step 2. After removing the catalyst by filtration, an equimolar amount of sulfuric acid is added. After reduction and mixing with a little ethanol, the product is precipitated out in the form of beige crystals with a melting point of 177°–179° C.

$^1$H-NMR (DMSO-d$_6$, 60 MHz): $\delta=7.70$ (s, wide 5H, NH, NH$_2$, H$_2$SO$_4$, exchangeable with D$_2$O), 7.30 (s, 1H, 3-H) and 4.00 ppm (m, 4H,—CH$_2$—CH$_2$—)

MS (70 eV): m/e=124 (M+)

EXAMPLE 3

Production of 3-amino-6-methyl-4,5,6,7-tetrahydropyrazolo[1,5-a]pyrimidine

Step 1: Synthesis of 3-nitro-6-methyl-4,5,6,7-tetrahydropyrazolo[1,5-a]pyrimidine The reaction is carried out as in Example 1, Step 1, with 1-bromo-3-chloro-2-methylpropane as alkylating agent. Yellow crystals with a melting point of 190°–192° C. are obtained in a yield of 25%.

$^1$H-NMR (DMSO-d$_6$, 60 MHz): $\delta=7.92$ (s, 1H, —NH, exchangeable with D$_2$O), 7.84 (s, 1H, 2-CH), 4.07 (m, 1H, N—CH$_2$—), 3.59 (m, 1H, N—CH$_2$), 3.38 ( m, 1H, N—CH$_2$—), 2.98 (m, 1H, NH—CH$_2$), 2.20 (m, 1H, 6C—H) and 1.02 ppm (d, 3H, J=7 Hz, 6C—CH$_3$).

MS (70 eV): m/e=182 (M+)

Step 2: Synthesis of 3-amino-6-methyl-4,5,6,7-tetrahydropyrazolo[1,5-a]pyrimidine sulfate After catalytic reduction and mixing of the reaction mixture with sulfuric acid corresponding to Example 1, Step 2, the sulfate is obtained in the form of colorless crystals with a melting point of 170° C. and a yield of 88 percent.

$^1$H-NMR (DMSO-d$_6$, 60 MHz): $\delta=7.40$ ppm (s, 5H, NH$_2$, NH, H$_2$SO$_4$(exchangeable with D$_2$O), 7.23 (s, 1H, 2C—H), 4.25-1.80 (m, 5H, —CH$_2$CH—CH$_2$), 0.97 ppm (d, J=7 Hz, 6C—CH$_3$)

MS (70 eV): m/e=152 (M+)

EXAMPLES FOR HAIR DYE COMPOSITION

EXAMPLE 3

Hair dye composition in gel form

| | |
|---|---|
| 1.00 g | 3-amino-4,5,6,7-tetrahydropyrazolo[1,5-a] pyrimidine sulfate |
| 0.50 g | 5-amino-2-methylphenol |
| 0.15 g | sodium sulfite, anhydrous |
| 5.00 g | lauryl alcohol diglycol ether sulfate sodium salt (28-percent aqueous solution) |
| 1.00 g | hydroxyethyl cellulose, highly viscous |
| 10.00 g | ammonia (22-percent aqueous solution) |
| 82.35 g | water |
| 100.00 g | |

50 g of the hair dye composition described above are mixed with 50 g hydrogen peroxide solution (6-percent) shortly before use. The mixture is then applied to blond natural hair and allowed to act for a period of 30 minutes at 40° C. The hair is then rinsed with water and dried. The hair has an intensive, purple-red coloring.

EXAMPLE 5

Hair dye composition in gel form

| | |
|---|---|
| 0.55 g | 3-amino-2,3-dihydro-1H-imidazo[1,2-b]pyrazole hydrosulfate |
| 0.27 g | 3-aminophenol |
| 0.30 g | ascorbic acid |
| 15.00 g | oleic acid |
| 7.00 g | isopropanol |
| 10.00 g | ammonia (22-percent aqueous solution) |
| 66.88 g | water |
| 100.00 g | |

Shortly before use, 50 g of this hair dye composition are mixed with 50 g hydrogen peroxide solution (6-percent) and the mixture is allowed to act on white human hair for 30 minutes at 40° C. The hair is then rinsed with water and dried. The hair is dyed a red-violet shade.

EXAMPLE 6

Dye composition in gel form

| | |
|---|---|
| 1.05 g | 3-amino-4,5,6,7-tetrahydropyrazolo[1,5-a]pyrimidine sulfate |
| 0.80 g | 2,5-diaminotoluene sulfate |
| 1.70 g | 2-amino-4-(2'-hydroxyethyl)amino anisole sulfate |
| 0.10 g | 1-(2'-ureidoethyl)amino-4-nitrobenzene |
| 0.15 g | sodium sulfite, anhydrous |
| 2.50 g | lauryl alcohol diglycol ether sulfate sodium salt (28-percent aqueous solution) |
| 0.80 g | hydroxyethyl cellulose, highly viscous |
| 6.00 g | ammonia, (22-percent aqueous solution) |
| 86.90 g | water |
| 100.00 g | |

50 g of the hair dye composition described above are mixed with 50 g hydrogen peroxide solution (6-percent) shortly before use. The mixture is then applied to blond natural hair and allowed to act for a period of 30 minutes at 40° C. The hair is then rinsed with water and dried. The hair has taken on an eggplant-like coloring.

EXAMPLE 7

Hair dye composition in gel form

| | |
|---|---|
| 1.05 g | 3-amino-6-methyl-4,5,6,7-tetrahydropyrazolo[1,5-a]pyrimidine sulfate |
| 0.40 g | 5-amino-2-methylphenol |
| 0.12 g | 3-aminophenol |
| 0.15 g | sodium sulfite, anhydrous |
| 5.00 g | lauryl alcohol diglycol ether sulfate sodium salt (28-percent aqueous solution) |
| 1.00 g | hydroxyethyl cellulose, highly viscous |
| 10.00 g | ammonia, (22-percent aqueous solution) |
| 82.28 g | water |
| 100.00 g | |

50 g of the hair dye composition described above are mixed with 50 g hydrogen peroxide solution (6-percent) shortly before use. The mixture is then applied to blond natural hair and allowed to act for a period of 30 minutes at 40° C. The hair is then rinsed with water and dried. The hair has taken on an intensive Bordeaux shade.

We claim:

1. Pyrazole derivative of the formula (II)

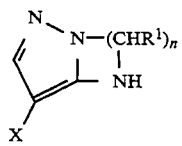

wherein $R^1$ is selected from the group consisting of hydrogen and alkyl groups having one to four carbon atoms; and wherein n=2 and X=is an amino group or n=3 and X is selected from the group consisting of nitro and amine groups.

2. Pyrazole derivative as defined in claim 1, consisting of 7-amino-2,3-dihydro-1H-imidazo]1,2-b]pyrazole.

3. Pyrazole derivative as defined in claim 1, consisting of 3-nitro-4,5,6,7-tetrahydropyrazolo-[1,5-a]pyrimidine.

4. Pyrazole derivative as defined in claim 1, consisting of 3-amino-4,5,6,7-tetrahydro-pyrazolo-[1,5-a]pyrimidine.

5. Pyrazole derivative as defined in claim 1, consisting of 3-nitro-6-methyl-4,5,6,7-tetrahydropyrazolo-[1,5-a]pyrimidine.

6. Pyrazole derivative as defined in claim 1, consisting of 3-amino-6-methyl-4,5,6,7-tetrahydro-pyrazolo-[1,5-a]pyrimidine.

7. Composition for oxidative dyeing of hair containing at least one coupler and 0.01 to 3.0 percent by weight of at least one developer, wherein said at least one developer is selected from the group consisting of aminopyrazole derivatives of the formula (I):

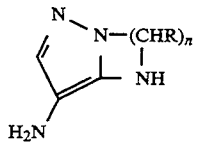

wherein R is selected from the group consisting of hydrogen and alkyl groups having one to four carbon atoms;

n=2 or 3;

and physiologically tolerated, water-soluble salts thereof;

wherein said at least one coupler is selected from the group consisting of resorcinol, 4-chlororesorcinol, 4,6-dichlororesorcinol, 2-methylresorcinol, 2-amino-4-(2'-hydroxyethyl)aminoanisole, 2,4-diaminobenzyl alcohol, 2,4-diaminophenylethyl alcohol, m-phenylenediamine, 2,4-diamino-5-(2'-hydroxyethoxy)toluene, 5-amino-2-methylphenol, 5-amino-4-fluoro-2-methylphenol, 5-amino-2-ethyl-4-fluorophenol, 5-amino-4-methoxy-2-methylphenol, 2,4-diaminophenoxyethanol, 4-amino-2-hydroxy-phenoxyethanol, 1-napthol, 3-aminophenol, 3-amino-2-methylphenol, 4-hydroxy-1,2-methylenedioxybenzene, 4-amino-1,2-methylenedioxybenzene, 4-(2'-hydroxyethyl)amino-1,2-methylenedioxybenzene, 2,4-diaminophenetole, 2,4-diamino-5-methylphenetole, 4-hydroxyindole, 3-amino-5-hydroxy-2,6-dimethoxypyridine and 3,5-diamino-2,6-dimethoxypyridine; and wherein said at least one developer and said at least one coupler are present in a total amount of from 0.1 to 5.0 percent.

8. Composition as defined in claim 7, wherein said aminopyrazole derivative is selected from the group consisting of 3-amino-4,5,6,7-tetrahydropyrazolo[1,5-a]pyrimidine, 7-amino-2,3-dihydro-1H-imidazo[1,2-b]pyrazole and 3-amino-6-methyl-4,5,6,7-tetrahydropyrazolo[1,5-a]pyrimidine.

9. Composition as defined in claim 7, wherein said at least one developer and said at least one coupler are present in a total amount of 0.5 to 4.0 percent.

10. Composition as defined in claim 7, further comprising another dye component selected from the group consisting of 6-amino-2-methylphenol, 2-amino-5-methylphenol, 4-[(4'-aminophenyl)-(4''-imino-2'',5''-cyclohexadinene-1''-ylidene)-methyl-2-methyl-aminobenzene monohydrocholoride; 4-(4'-amino-3'-methylphenyl)-(4''-imino-3''methyl-2'',5''-cyclohexadiene-1''-ylidene-methyl[-2-methyl-aminobenzenemonohydrochloride, 2-nitro-1,4-diaminobenzene, 2-amino-4-nitrophenol, 2-amino-5-nitrophenol, 2-amino-4,6-dinitrophenol, 2-amino-5-(2'-hydroxyethyl)aminonitrobenzene, 2-methylamino-5-bis(2'-hydroxyethyl)aminonitrobenzene, sodium salt of 7-[4''-amino-phenylazo]-8-hydroxy-naphthaline-4-sulfonic acid, 1,4-diaminoanthraquinone and 1,4,5,8-tetraamino-anthraquinone.

11. Pyrazole derivative of the formula (II)

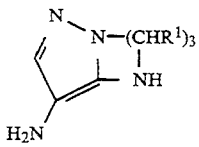

(II)

where $R^1$ selected from the group consisting of hydrogen and alkyl groups having one to four carbon atoms.

12. Composition for oxidative dyeing of hair containing at least one coupler and 0.01 to 3.0 percent by weight of at least one developer, wherein said at least one developer is selected from the group consisting of aminopyrazole derivatives of the formula (I):

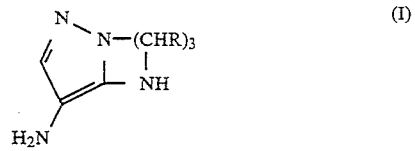

(I)

wherein R is selected from the group consisting of hydrogen and alkyl groups having one to four carbon atoms;

and physiologically tolerated, water-soluble salts thereof;

wherein said at least one coupler is selected from the group consisting of resorcinol, 4-chlororesorcinol, 4,6-dichlororesorcinol, 2-methylresorcinol, 2-amino-4-(2'-hydroxyethyl)aminoanisole, 2,4-diaminobenzyl alcohol, 2,4-diaminophenylethyl alcohol, m-phenylenediamine, 2,4-diamino-5-(2'-hydroxyethoxy)toluene, 5-amino-2-methylphenol, 5-amino-4-fluoro-2-methylphenol, 5-amino-2-ethyl-4-fluorophenol, 5-amino-4-methoxy-2-methylphenol, 2,4-diaminophenoxyethanol, 4-amino-2-hydroxy-phenoxyethanol, 1-napthol, 3-aminophenol, 3-amino-2-methylphenol, 4-hydroxy-1,2-methylenedioxybenzene, 4-amino-1,2-methylenedioxybenzene, 4-(2'-hydroxyethyl)amino-1,2-methylenedioxybenzene, 2,4-diaminophenetole, 2,4-diamino-5-methylphenetole, 4-hydroxyindole, 3-amino-5-hydroxy-2,6-dimethoxypyridine and 3,5-diamino-2,6-dimethoxypyridine; and wherein said at least one developer and said at least one coupler are present in a total amount of from 0.1 to 5.0 percent.

13. Composition as defined in claim 12 wherein said physiological tolerated water-soluble salts are selected from the group consisting of hydrochloric acid salts of said aminopyrazole derivatives and sulfuric acid salts of said aminopyrazole derivatives.

* * * * *